(12) United States Patent
Roy et al.

(10) Patent No.: US 9,763,881 B2
(45) Date of Patent: Sep. 19, 2017

(54) RICE BRAN-LIPIDS BASED FORMULATION AND PROCESS FOR PREPARATION THEREOF FOR SELECTIVE DELIVERY OF GENES TO CANCER CELLS

(71) Applicant: Council Of Scientific And Industrial Research, New Delhi (IN)

(72) Inventors: Sayantani Roy, Hyderabad (IN); Rajkumar Banerjee, Hyderabad (IN); Pradosh Prasad Chakrabarti, Hyderabad (IN); Badari Narayana Prasad Rachapudi, Hyderabad (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/406,895

(22) PCT Filed: Jun. 11, 2013

(86) PCT No.: PCT/IN2013/000368
§ 371 (c)(1),
(2) Date: Dec. 10, 2014

(87) PCT Pub. No.: WO2013/186793
PCT Pub. Date: Dec. 19, 2013

(65) Prior Publication Data
US 2015/0164797 A1 Jun. 18, 2015

(30) Foreign Application Priority Data
Jun. 11, 2012 (IN) .......................... 1792/DEL/2012

(51) Int. Cl.
| | | |
|---|---|---|
| *A61K 9/127* | (2006.01) | |
| *A61K 38/17* | (2006.01) | |
| *A61K 38/18* | (2006.01) | |
| *A61K 38/19* | (2006.01) | |
| *A61K 38/45* | (2006.01) | |
| *A61K 38/50* | (2006.01) | |
| *A61K 47/44* | (2017.01) | |
| *A61K 47/24* | (2006.01) | |
| *A61K 48/00* | (2006.01) | |

(52) U.S. Cl.
CPC ............ *A61K 9/127* (2013.01); *A61K 9/1272* (2013.01); *A61K 9/1277* (2013.01); *A61K 38/1758* (2013.01); *A61K 38/1841* (2013.01); *A61K 38/191* (2013.01); *A61K 38/45* (2013.01); *A61K 38/50* (2013.01); *A61K 47/44* (2013.01); *A61K 47/24* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 5,871,714 | A | 2/1999 | Budny |
| 5,900,366 | A | 5/1999 | Marchal et al. |
| 6,333,433 | B1 | 12/2001 | Banerjee et al. |
| 6,346,516 | B1 | 2/2002 | Banerjee et al. |
| 6,503,945 | B2 | 1/2003 | Banerjee et al. |
| 6,541,649 | B2 | 4/2003 | Banerjee et al. |
| 6,953,849 | B2 | 10/2005 | Vali et al. |
| 2011/0293695 | A1* | 12/2011 | Panzner ............... A61K 9/1272 424/450 |

FOREIGN PATENT DOCUMENTS

| | | |
|---|---|---|
| EP | 0893493 A2 | 1/1999 |
| JP | 10152498 A | 1/1998 |
| JP | 11106395 A | 4/1999 |
| WO | WO 99/00136 | 1/1999 |
| WO | WO 99/12562 | 3/1999 |

OTHER PUBLICATIONS

Ewert, et al. (2010) "Cationic Lipid—Nucleic Acid Complexes for Gene Delivery and Silencing: Pathways and Mechanisms for Plasmid DNA and siRNA". Topics in Current Chemistry, 296: 191-226, downloaded Jan. 21, 2016 as NIH public access document, 40 pages long.*

Alkhalaf, et al. (2003) "Overexpression of wild-type p53 gene renders MCF-7 breast cancer cells more sensitive to the antiproliferative effect of progesterone", Journal of Endocrinology, 179: 55-62.*

Onishi and Fujino (1978) "Novel Glycolipids; Cellobiosylsterol and Cellotriosylsterol in Rice Bran", Agricultural and Biological Chemistry, 42(12): 2423-25.*

Spiegel, et al., "Grafting of triggering site onto lymphocytes; distribution of grafted dinitrophenyl groups on cell surface glycoproteins and glycolipids," *Mol. Cell. Biochem.*, 55(2):183-190 (1983).

Chaney, et al., "Interaction of gangliosides with B cells in splenic fragment cultures," *Cellular Immunology*, 86(1):165-170 (1984).

Gorio, et al., "Ganglioside Treatment of Genetic and Alloxan-Induced Diabetic Neuropathy," *Fidia Research Laboratories, Dept. of Cytopharm. And Biochem.*, 549-561 (1984).

Nilsson, et al., "Monoclonal antibodies raised against NeuAcα2-6neolactotetraosylceramide detect carcinoma-associated gangliosides," *Biochim. Biophys, Acta*, 835(3):577-583 (1985).

(Continued)

*Primary Examiner* — Robert M Kelly
(74) *Attorney, Agent, or Firm* — Brinks Gilson & Lione

(57) ABSTRACT

The present invention relates to a formulation in which glycolipids and phospholipids, isolated from rice bran gum samples, were used in conjunction with gene carrying lipids to test its efficacy in delivering genes to cancer cells selectively. This formulation did not mediate efficient delivery of genes to non-cancerous cells, thus, showing potential use of this formulation to deliver anticancer therapeutics to cancer cells without eliciting treatment related toxicity to normal cells.

8 Claims, 5 Drawing Sheets

(56) References Cited

OTHER PUBLICATIONS

Figure 1:
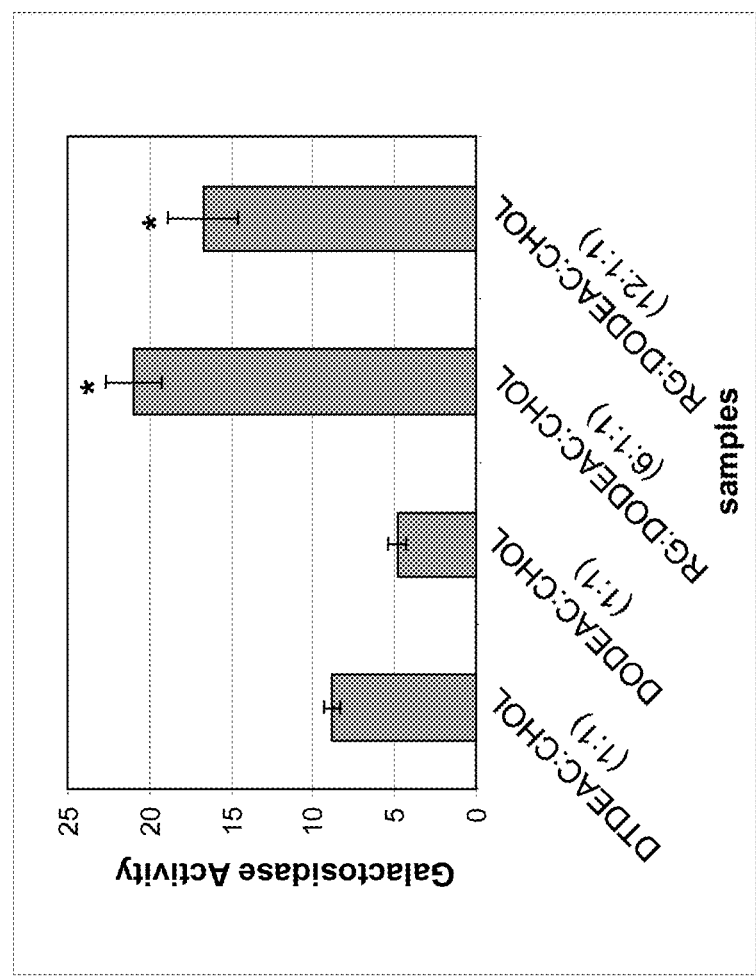

Park, et al., "Innate and adaptive functions of the CD1 pathway of antigen presentation," *Immunology*, 10:391-398 (1998).
Moody, et al., "The molecular basis of CD1-mediated presentation of lipid antigens," *Immunology* Reviews, 172:285-296 (1999).
Hammache, et al., "Sequential Interaction of CD4 and HIV-1 gp 120 with a reconstituted membrane patch of ganglioside GM3:implications for the role of glycolipids as potential HIV-1 fusion cofactors," *Biochem, Biophys. Res. Commun.*, 246(1):117-122 (1998).
Koso, "Protein, Nucleic acid, enzyme," *TAKKAJ*, 43(16):2582-2588 (1998).
Daniel, et al., "Production of sophorolipds from whey: development of a two-stage process with *Cryptococcus curvatus* ATCC 20509 and *Candida bombicola* ATCC 22214 using deproteinized whey concentrates as substrates," Applied Microbiology And Biotechnology, 51:40-45 (1999).
Sholtz, et al., "Bioactivity of extracellular glycolipids—Investigation of potential anti-cancer activity of Sophorolipids and Sophorolipid-derivatives," *Polym, Prepr.*, 39(2):168-169 (1998).
Schmidt, et al., "*Plasmodium falciparum*: Asexual Erythrocytic Stages Synthesize Two Structurally Distinct Free and Protein-Bound Glycosylphosphatidylinositols in a Maturation-Dependent Manner," *Exp. Parasitol.*, 88:95-102 (1998).
Harder and Simons, "Clusters of glycolipid and glycosylphosphatidylinositol-anchored proteins in lymphoid cells: accumulation of actin regulated by local tyrosine phosphyorylation," *Eur., J. Immunol*, 29:556-562 (1999).
Hansson, et al., "Mouse Monoclonal Antibodies against Human Cancer Cell Lines with Specificities for Blood Group and Related Antigens," *J. Biol. Chem.*, 258(7):4091-4097 (1983).
Curatolo, "Glycolipid Function," *Biochimica et Biophysica Acta*, 906:137-160 (1987).
Besancon, "Binding of interferon to gangliosides," *Nature*, 252:478-480 (1974).
Parker et al, "Binding of interleukin 2 to gangliosides," *FEBS 1466*, 170(2):391-395 (1984).
Spiegel et al., "Involvement of gangliosides in lymphocyte stimulation," *Proc. Natl. Acad. Sci. USA*, 76(10):5277-5281 (1979).
Spiegel and Wilcheck, "Rice bran-lipids based formulation and process for preparation thereof for selective delivery of genes to cancer cells WO 2013186793A1," *M. J. Immunol*, 127:572-575 (1981).
Miller and Esselman, "Modulation of the Immune Response by Antigen-Reactive Lymphocytes After Cultivation With Gangliosides," *J. Immunol.* 115(3):839-843 (1975).
Ladisch et al., "Shedding and Immunoregulatory Activity of YAC-1 Lymphoma Cell Gangliosides," *Cancer Research*, 43:3808-3813 (1983).
Purpura and Baker, "Meganeurites and Other Aberrant Processes of Neurons in Feline $G_{M1}$-Gangliosidosis: A Golgi Study," *Brain Res.*, 143:13-26 (1977).
Byrne et al., "Ganglioside-Induced Neuritogenesis: Verification That Gangliosides Are the Active Agents, and Comparison of Molecular Species," *J. of Neurochem.*, 41:1214-1222 (1983).
Hakomori, "Structures and Organization of Cell Surface Glycolipids Dependency on Cell Growth and Malignant Transformation," *Biochimica et Biophysica Acta*, 417:55-89 (1975).
Feizi, "Demonstration by monoclonal antibodies that carbohydrate structures of glycoproteins and glycolipids are onco-developmental antigens," *Nature*, 314:53-57 (1985).
Hakomori and Murakami, *Proc. Natl. Acad. Sci., USA*, 59:254-261 (1967).
Ogiso, "Implication of glycolipids in lens fiber development," *Acta, Biochimica Polonica*, 45(2):501-507 (1998).
Daniel et al., "Production of sophorolipds in high concentration from deproteinized whey and rapeseed oil in a two stage fed batch process using *Candida bombicola* ATCC 22214 and *Cryptococcus curvatus* ATCC 20509," *Biotechnol. Lett.*, 20(12):1153-1156 (1998).
Roberts et al., "Growth factor-induced release of a glycosyl-phosphatidylinositol (GPI)-linked protein from the HEp-2 human carcinoma cell line," *FEBS Lett.* 08592, 267(2):213-216 (1990).
Kitamoto et. al., "Functions and Potential Applications of Glycolipid Biosurfactants—from Energy-Saving Materials to Gene Delivery Carriers," *J. Bioscience and Bioengineering*, 94(3):187-201 (2002).
Hemavathy and Prabhakar, "Lipid Composition of Rice (*Oryza sativa* L.) Bran," JAOCS, 64(7):1016-1019 (1987).
Hansson, et al., "Mouse Monoclonal Antibodies against Human Cancer Cell Lines with Specificities for Blood Group and Related Antigens," *J. Biological Chemistry*, 258(7):4091-4097 (1983).

* cited by examiner

RICE BRAN-LIPIDS BASED FORMULATION AND PROCESS FOR PREPARATION THEREOF FOR SELECTIVE DELIVERY OF GENES TO CANCER CELLS

RELATED APPLICATIONS

The present patent document is a §371 filing based on PCT Application Serial No. PCT/IN2013/000368, filed Jun. 11, 2013, designating the United States and published in English, which claims priority from Indian application number 1792/DEL/2012, filed on Jun. 11, 2012. All of the foregoing applications are hereby incorporated by reference.

The following specification describes the invention and the manner in which it is to be performed

FIELD OF THE INVENTION

The present invention relates rice bran-lipids based formulation and process for preparation thereof for selective delivery of genes to cancer cells. Particularly, the present invention provides a formulation in which glycolipids and phospholipids, isolated from rice bran gum samples, were used in conjunction with gene carrying lipids to deliver genes to cancer cells selectively. The present invention also relates to non-viral delivery of genetic products selectively to cancer cells. The present invention more particularly relates to delivery of genetic products selectively to cancer cells whose certain cell-surface receptorshave probable affinity to the rice-bran glycolipids or phospholipid mixtures.

BACKGROUND OF THE INVENTION AND DESCRIPTION OF PRIOR ART

Glycolipids are known to affect four general functions related to cell membranes; stabilization, shape determination, recognition and ion-binding (Curatoto, W: Biochim. Biophys. Acta, 906, 1987, 137-160). Glycolipids are also implicated for various immunological phenomena. The interference of gangliosides in the action, of interferon was reported in early seventies (Bensancon, F. and Ankel, I I Nature, 252, 1974, 478-480). Interleukin-2 was found to have affinity towards gangliosides (Parker, J., et at, FEBS Lett., 170, 1984, 391-395). It has been reported that the involvement of glycolipids in lymphocyte stimulation (Spiegel, S., et al., Proc. Natl. Acad. Sci., 76, 1979, 5277-5281; Spiegel, S and Wilchesk, M. J. Immunol, 127, 1981, 572-575; Spiegel, S. and Witcheck, M., Mol. Cell. Biochem. 55, 1983, 183-190). It was suggested that gangliosides might be involved in immuno regulations (Miller, H. C. and Essenman, W. J., J. Immunol. 115, 1975, 839-843); Chaney, W. G. et. al. Cell Immunol. 86, 1984, 165-170). The possibilities of immunosuppressive effects of gangliosides from tumor cells were also reported (Ladish, S, et. al., Cancer Research, 43, 1983, 3808-3813), Gangliosides are also known to have significant impact in the growth of neurons. A group of scientists reported that proliferation of neurites of felines with gangliosidosis was observed (Purpura, D. P. and Baker, H. J Brain Res., 143, 1978, 13-26). Later, these effects were elicited by various purified ganglioslides (Byrene, M. C., et al, J. Neurochem., 41, 1983, 1214-1222). These in vitro results were utilized for curing neuropathies with ganglioside injections (Gorio, A. et al, in Ganglioside Structure, Function and Biomedical Potential, Ed. by Ledeen, R, Yu, R, Raport, M and Suzuki, K. Plenum Press, New York, 1984, 549-561). Clinical trials on human volunteers showed that ganglioside injections improve symptoms of diabetic neuropathy (Narden, A., et al., in Ganglioside Structure, Functions and Biomedical Potential, ed. By Ledeen, R, Yu, R., Rapoort, M and Suzuki, K, Plenum Press, New York, 1984, 593-600). In oncogenesis also, glycolipids play an significant role. It was observed that qualitative and quantitative changes in the cell glycolipids occur during differentiation and oncogenesis (Hakomori, S. Biochim. Biophysm Acta, 417, 1975, 55 89; Feizi, T.; Nature, 314, 1985, 53-57). The glycolipids from the tissues of the tumors found to have both qualitative and quantitative differences with normal tissues (Hamomori, S. and Murakami, W. T., Proc. Natl. Acad. Sci., USA, 59, 1968, 254-261). Different antibodies were used to characterize a number of tumor antigens on gangliosides (Tai, T., et al., Biochim. Biophys, Acta, 835, 1985, 577-583) and on neutral glycosphingolipids (Willson, K. R., et al. J. Biol. Chem, 1983, 4091-4097). These studies of glycolipid antigens on cell surfaces have generated significant information regarding glycolipid synthesis and the nature of the cell surface in differentiation and oncogenesis.

In recent years, many researchers have shifted their focus to understand the possible mechanisms of regulating various physiological phenomena by glycolipids. Biological activities of glycolipids isolated from various natural resources are being evaluated. Scientists are also checking the suitability of use of glycolipids in pharmaceutical and cosmetic formulations. The use of glycolipids from sivers sagebrush (wormwood) as organoleptic and biologically active additive in food industries were tested (Gubanenko, G. A., et al, Pischch. Prom. St. 6, 1998, 26-27). The possible role of glycolipids in type 1 diabetes and lupus, in intracellular bacterial infections and in tumor rejections were also investigated (Park, S. II. et al, Semin. Immunol., 10(5), 1998, 391-398). Biological activities of some natural and synthetic glycolipid antigens that induce a CD-1 restricted 1-cell response are described in PCT Int, Appl. WO 99, 12562 (Porcelli, S. A. and Moody, D. B., 1999). Glycolipids of these kinds were used for treatment of people infected with *Mycobacterium leparae*. Glycolipids also have an important role in lens fiber developed in human eye (Ogiso, M, Acta, Biochim. Pol., 45 (20, 1998, 501-507).

The transfection efficiency and cell uptake of DNA/ glycolipid complexes were considered as potential HIV-1 fusion cofactor (Djilalj, H., et al, Biochim, Biophys. Res. Commun. 246(1), 1998, 117-122). Glycolipid-based compositions were used for controlling of colonization of bacterial plaque in the oral cavity (Bundy, J. A. U.S. Pat. No. 5,871,714, 1999). Another formulation consisting of glycolipids was used in treatment for prophylaxis or acidic gut syndrome (Rowe, J. B., PCT Int. Appl. WO 99, 00136, 1999). The role of glycolipids on age related changes of the brain as well as in Alzheimer's disease was examined in a recent review (Endo, T. Tampakskitu Kakusan Koso, 43 (16), 1998, 2582-2588). Sophorolipids were isolated from various sources (Marchal, R., et al., U.S. Pat. No. 5,900,366, 1999: Daniel; H. S. et al, Biotechnol., 51 (1), 1999, 40-45) including from deproteinized whey and rapeseed oil (Daniel, H. S., et al, Biotechnol, Lett, 29(12), 1998, 1153-1156). Bioactivity of these sophorolipids and sophorolipid-derivatives were evaluated (Sholtz., C., et al., Polym, Prepr. 39 (2), 1998, 168-169). It was observed that glycolipids like sophorolipids exhibit cell growth inhibition properties for. Jurkat (Leukemia) and Tu-138 (head and neck cancer) cells. Glycosylphosphatidyl inositols have an effect on material toxins and in release of cytokines like tumor necrosis factor- and interleukin-10 (Schmidt, A., et at, Exp. Parasitol., 88(2)., 1998, 95-102).

In the late nineties, a group of scientists isolated a new glycolipid from *Gigartina tenella* (Ohra K, et al., Jpn. Kokai Tokkyo Koho, JP 11, 106, 395, 1999). This glycolipid was found to have high activity as DNA-synthetase B-inhibitor, HIV inhibitor and as immunosuppressant. It was also found that these glycolipids can act as anti-cancer agents and have other immunosuppressive effects (Yoshida, M., et al., Jpn Kokai Tokkyo Koho J P, 10, 152, 498, 1998). The cellular responses of Clusters of glycolipids and glycosyl-phosphatidyl inositol-anchor proteins in lymphoid cells towards raft patch formation in the Jurkat (Leukemia) T-cell lines were investigated (Harder, T. and Simons, K., Eur., J. Immunol, 29 (2), 1999, 556-562). Growth factor-induced release of a glycosyl-phosphatidyl inositol (GPI)-linked protein from HEP-G2 human carcinoma cell lines was examined earlier (Roberts, J. M., et, al., FEBS Lett., 267 (2), 267 (2), 1996, 213-216). The possible use of glycolipids in gene therapy was also tested (Havermann, K., et. al, EP 893,493, 1999).

It is surprising that these compounds are not exploited commercially though they have such diversified functions and biological activities. The most probable reasons could be the lack of availability of natural sources rich in glycolipids or may be non availability of commercially viable processes for their isolation. Rice bran oil may offer significant possibilities as its glycolipids content was found to be quite high. Earlier, a process was developed in this laboratory to isolate and purify glycolipids from rice bran oil [Vali et. al. U.S. Pat. No. 6,953,849 (2005)].

In this present invention, glycolipids and phospholipids isolated from rice bran oil gums were used either separately or in combination to prepare a non-viral formulation for a potent carrier to deliver anti-cancer genes Et bioactive compounds to breast and lung cancer cells. There is an example of glycolipids (mannosylerythritol) originally isolated from *Candida antarctica* that was being supplemented in a cationic lipid formulation for the purpose of gene delivery to mammalian cells. (Kitamoto et. al. J. Bioscience and Bioengineering, 2002, 94, 187-201). The major components present in rice bran glycolipids are acylated steryl glucoside (ASG), digalactosyldiatyl glycerol (DGDG) and monogatactosylnionoacylglycerot (MGMG). The major components of rice bran phospholipids are phosphatidyl choline (PC), phosphatidyl ethanolamine (PE), phosphatidyl inositol (PI) and phosphatidic acid (PA) (Hemavathy J and Prabhakar J V, J. Amer. Oil Chem. Soc., 1987, 64, 1016-1019).

In the present invention, the glycolipid and phospholipids are either individually associated with respective cationic lipid formulation or they are supplemented to the cationic liposomal formulation in the form of cocktail mixture. This not only increased the transfection efficacy of cationic lipid but also the new formulation mediated gene transfer to cancer cells only. The same glycolipid/phospholipid associated or supplemented cationic liposomal formulation did not show efficient transfection in cells with no cancer lineage. This potent liposomal formulation can be used for specific delivery of anticancer therapeutics such as anticancer genes to cancer cells only without eliciting any treatment related toxicity to normal cells.

Chemotherapy and radiation therapies are two current clinical modalities commonly used for the treatment of cancer. Mostly these techniques are effective to block the growth of tumor; however, there is often a recurrence of the disease, possibly because of incomplete cell killing or cells acquiring drug resistance. Moreover, none of the current treatment modalities are hundred non-toxic to normal cells and are often deleterious to general health.

In comparison to the non-viral gene delivery method as depicted in the present invention, the viral based gene delivery is also quite well known and is extensively investigated utilizing their phenomenally efficient process of delivering genes to wide variety of cells. A number of problems including host toxicity, immunogenic responses and non-specific genomic integration of transferred gene make viral delivery a risky option for delivering genes. In comparison, non-viral gene delivery is a much more robust and clinically safe option compared to viral counterparts. The patented cationic lipid, DODEAC [Banerjee et. al. U.S. Pat. No. 6,333,433 B1 (2001), U.S. Pat. No. 6,346,516 B1 (2002), U.S. Pat. No. 6,503,945 (2003a), U.S. Pat. No. 6,541,649 (2003b)], whose structure is. N,N-dihydroxy-ethyl, N,N-dioctadecyl, ammonium chloride forms cationic liposome using co-lipid cholesterol in membrane filtered water. This product has been, used for the transfection of DNA into cultured eukaryotic cells of various origins. However, the formulation, in spite of exhibiting moderate transfection of genes to all cells irrespective of origin, shows no specific targeting of genes to cancer cells. Towards this end, the present invention relates to development of a new rice-bran isolated glycolipid/phospholipid carrying cationic lipid based formulation, which targets and deliver genes to breast and lung cancer cells alone. The idea of making this formulation stems from the fact that glycolipids, which has close structural resemblance with galactosyl- or other carbohydrate ligands that show highly selective affinity to asialoglycoprotein or other carbohydrate receptors that are avidly expressed in various cancer cells.

OBJECTS OF THE INVENTION

The main object of the present invention is to provide rice bran-lipids based formulation and process for preparation thereof for selective delivery of genes to cancer cells.

Another object of the present invention is to co-formulate cationic lipid based gene delivery formulation carrying rice bran glycolipid/phospholipids based pharmacologic agents along with common co-lipid cholesterol.

Another object of the present invention is to provide a method for delivering genetic constructs via a non-viral method with enhanced efficiency by co-formulating cationic lipid based gene delivery formulation carrying rice bran glycolipid/phospholipids based pharmacologic agents along with common co-lipid cholesterol.

Still another object of the present invention is to bring about delivery of genetic products selectively to cancer cells whose certain cell-surface, receptors may have probable affinity to the rice-bran glycolipids or phospholipid mixtures.

Yet another object of the present invention is to provide a method of treating tumor cells by providing genes which induce greater cell death in combination with a glycolipid pharmacologic agent possessing anticancerous effects.

SUMMARY OF THE INVENTION

Accordingly, the present invention provides a liposomal formulation useful for selective targeting and delivery of genes or genetic products to cancer cells, comprising:
(a) a cationic lipid in the range of 7-40 mole % of all constituent lipids;
(b) a co-lipid in the range of 7-40 mole % of all constituent lipids, said co-lipid is characterized in facilitating successful intracellular delivery of the biologically active molecules such as genes and gene products;

(c) rice bran glycolipids and/or phospholipids as adjuvant lipids in the range of 20-85 mole % of all constituent lipids, wherein said glycolipids and/or phospholipids are characterized in enhancing the transfection efficiency of the formulation; and (d) a gene or genetic products of interest.

In an embodiment of the present invention the rice bran lipids are selected from either glycolipids or phospholipids alone or in combination.

In one embodiment of the present invention the cationic lipid is selected from the group consisting of DODEAC (N,N-di-n-octadecyl-N,N-dihydroxyethyl ammonium chloride, DOTAP (N-[1-(2,3-Dioleoyloxy)propyl]-N,N,N-trimethylammonium methylsulfate (or chloride), DMRIE (2,3-di(myristyloxy)propyl-[2-hydroxyethyl]-dimethylammonium bromide).

In another embodiment of the present invention the co-lipid used is natural sterols. In still another embodiment of the present invention the co-lipid used is cholesterol. In still another embodiment of the present invention the glycolipids and phospholipids used are isolated from rice, bran oil gums.

In still another embodiment of the present invention a formulation is useful for non viral delivery of genetic products selectively to cancer cells.

In still another embodiment of the present invention the genetic product is selected from the group consisting of p53, tumor necrosis' factor, thymidine kinase, cytosine deaminase, 5 E1A, and TGF-beta.

In still another embodiment of the present invention the cancer cells are selected from the group consisting of MCF-7 (breast), A549 (lung), PC-3 (prostate) and HT-29 (colon).

In still another embodiment of the present invention a process for the preparation of the formulation, wherein the said process comprising the steps of:

a) mixing glycolipids and phospholipids isolated from rice bran oil gums in a mole ratio of 1:1 in a solvent, preferably chloroform, followed by drying and thereafter suspending in water to obtain suspension of glycolipid-phospholipid cocktail (RG);

b) mixing cationic lipid, preferably DODEAC and a co-lipid, preferably cholesterol in a mole ratio of 1:1 in a solvent, preferably chloroform, followed by drying as a thin film by nitrogen flow for a period ranging between 10-15 min at temperature ranging between 25-30° C. and further drying under vacuum for a period ranging between 4-6 hrs to obtain dried lipid film;

c) hydrating the dried lipid film as obtained in step (b) by keeping dried film in water for a period ranging between 10-12 hrs followed by vortexing for a period ranging between 1-2 min and bath sonicating for a period ranging between 2-3 min and probe sonicating for a period ranging between 2-3 min at temperature ranging between 25-30° C.;

d) adding aqueous solution of a cationic lipid, as obtained in step (c), into the glycolipid-phospholipid cocktail (RG) as obtained in step (a) while maintaining the mole ratio of RG:cationic lipid:co-lipid in the range of 6:1:1 to 12:1:1 to obtain formulation;

e) alternatively, mixing cationic lipid, preferably DODEAC, a co-lipid, preferably cholesterol and glycolipid or phospholipid individually or glycolipid-phospholipid cocktail (RG) as obtained in step (a) in a mole ratio of 1:1:0.5 in a solvent, preferably chloroform, followed by drying as a thin film by nitrogen flow for a period ranging between 10-15 min at temperature ranging between 25-30° C. and further drying under vacuum for a period ranging between 4-6 hrs to obtain dried lipid film;

f) hydrating the dried lipid film as obtained in step (e) by keeping dried film in water for a period ranging between 10-12 hrs followed by vortexing for a period ranging between 1-2 min and bath sonicating for a period ranging between 2-3 min and probe sonicating for a period ranging between 2-3 min at temperature ranging between 25-30° C. to obtain formulation.

In still another embodiment of the present invention formulation is made optionally either with phospholipid or glycolipid alone or in combination

BRIEF DESCRIPTION OF DRAWINGS & FIGURES

FIG. 1 shows that RG:DODEAC:CHOL formulations could achieve more gene transfection in MCF-7 cells than when RG is not incorporated. The gene transfection by RG:DODEAC:CHOL formulations were even better than DTDEAC:CHOL (our previously patented formulation for efficient gene transfection). This indicates that by incorporation of rice bran glycolipid/phospholipid cocktail [RG] to DODEAC:CHOL formulation, the resulting formulations acquires significantly more gene transfecting ability than the basic formulation DODEAC:CHOL. Hence rice bran glycolipid/phospholipid cocktail probably has the ability to induce more gene transfection ability of cationic liposomes in cancer cells.

Figure 2:
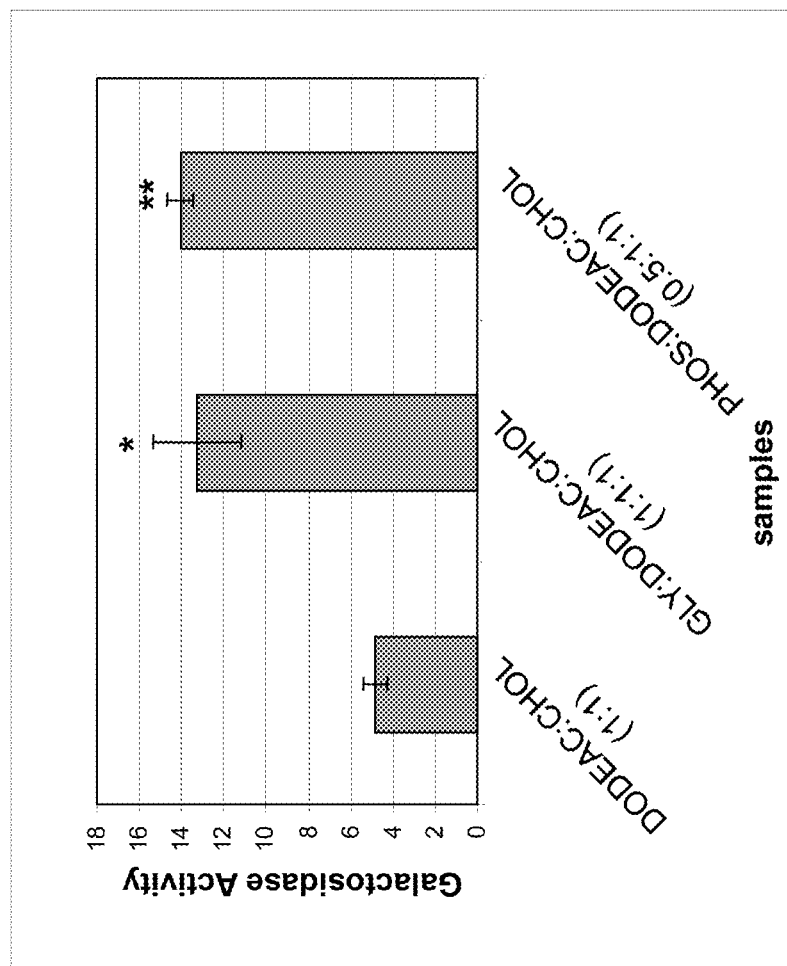
Figure 3:
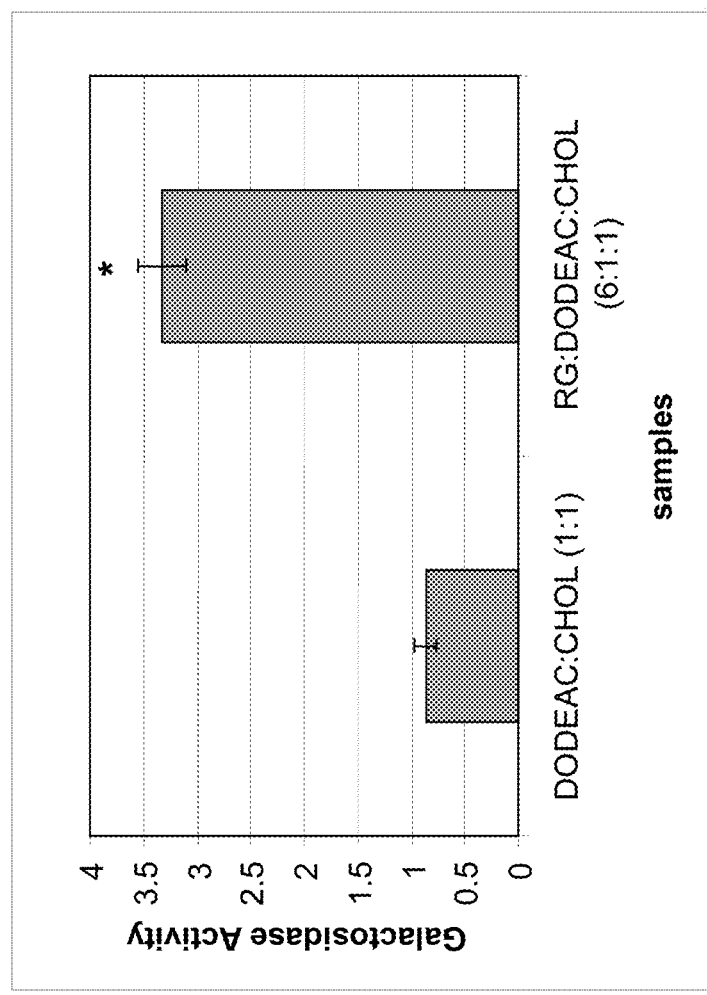
Figure 4:
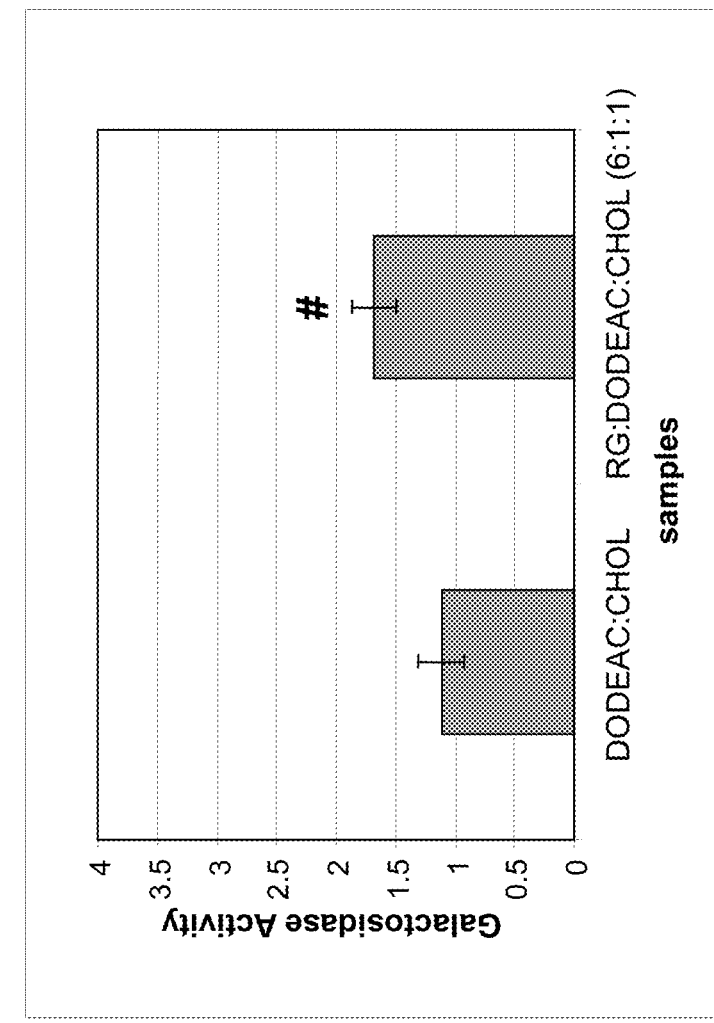

FIG. 2 shows that the preformed liposomal formulation containing either phospholipid or glycolipid along with DODEAC and CHOL [i.e, GLY:DODEAC:CHOL or PHOS: DODEAC:CHOL] has significantly more gene transfection ability in MCF-7 cancer cells than the transfection ability of basic DODEAC:CHOL formulation. So, the rice bran phospholipid or glycolipid has individual capability to induce more gene transfection ability of cationic liposomes in cancer cells FIG. 3 shows that RG:DODEAC:CHOL formulations could achieve more gene transfection in A549 lung cancer cells than when RG is not incorporated. The gene transfection by RG:DODEAC:CHOL formulations were even better than DTDEAC:CHOL (our previously patented formulation for efficient gene transfection). This indicates that by incorporation of rice bran glycolipid/phospholipid cocktail [RG] to DODEAC:CHOL formulation, the resulting formulations acquires significantly more gene transfecting ability than the basic formulation DODEAC:CHOL. Hence rice bran glycolipid/phospholipid cocktail probably has the ability to induce more gene transfection capability in cancer cells to cationic liposomes FIG. 4 shows that the association of glycolipid/phospholipid (RG) to cationic liposome did not impart any additional increase in gene transfection in non cancerous CHO cells. This shows that the RG has no specific affinity to non cancer, cells and hence is unable to provide any specific targeting or gene transfection enhancing ability to Liposomes against non cancer cells FIG. 5 exhibits that the enhanced transfection efficiency of RG associated lipid-DNA complex is maintained in the relevant physiological condition. Generally, in higher serum concentration, the lipid/DNA complex tend to collapse leading to decrease in gene transfection. This is not happening here in this case. This indicates that the RG-associated formulation maintains its cancer cell selectivity white maintaining its gene transfection efficiency.

ABBREVIATIONS

DODEAC: N,N-di-n-octadecyl-N,N-dihydroxyethyl ammonium chloride, DTDEAC: N,N-di-n-ditetradecyl-N,N-dihydroxyethyl ammonium chloride, DMEM: Dulbecco's Modified Eagle medium, CHOL: cholesterol, FBS: fetal bovine serum

DETAILED DESCRIPTION OF THE INVENTION

Glycolipids and phospholipids were isolated from rice bran oil as described in our previous patent [Vali et. al. U.S. Pat. No. 6,953,849 (2005). The rice bran oil sample used in this study was obtained as a gift sample from M/s. Ramcharan Oil Industries, Hyderabad.

The present invention relates to a method for delivering genes or genetic products or genetic constructs via a non-viral mode with enhanced efficiency by co-formulating cationic lipid based gene delivery formulation carrying rice bran glycolipid/phospholipids based pharmacologic agent along with common co-lipid cholesterol.

The invention provides novel formulation comprising optimal amounts of the cationic lipid, rice bran glycolipid/phospholipids pharmacologic agent and the co-lipid. One or more additional physiologically acceptable substances such as cetrimide, cetyl pyridinium chloride may be included in the pharmaceutical formulation of the invention to stabilize the formulation for storage or to facilitate successful intracellular delivery of the biologically active molecules. Co-lipids according to the practice of the present invention are, useful in mixing with cationic lipid. Cholesterol is an excellent co-lipid for use in combination with the cationic lipid DODEAC (N,N-di-n-octadecyl-N,N-dihydroxyethyl ammonium chloride) is used to facilitate successful intracellular delivery of the biologically active molecules. On fixing the mole-concentration of cationic lipid (DODEAC) and cholesterol, the mole-concentration of glycolipid and/or phospholipid changed from 0 to 20 mole equivalents. As such, it is within the art to vary the said range to a considerably wide extent. Typically, liposomes were prepared by dissolving DODEAC and the co-lipid (Cholesterol) without or with glycolipid and/or phospholipids in the appropriate mole ratio in a mixture of methanol and chloroform in a glass vial. The solvent was removed with a thin flow of moisture free nitrogen gas and the dried lipid film was then kept under high vacuum for 8 h. The dried lipid film was hydrated in sterile deionized water in a total volume of 1 mL at cationic lipid concentration of 1 mM for a minimum of 12 h. Liposomes were vortexed for 1-2 minutes to remove any adhering lipid film and sonicated in a bath sonicator (ULTRAsonik 28X) for 2-3 minutes at room temperature to produce multilamellar vesicles (MLV). MLVs were then sonicated with a Ti-probe (using a Branson 450 sonifier at 100% duty cycle and 25 W output power) for 1-2 minutes to produce small unilamellar vesicles (SUVs) as indicated by the formation of a clear translucent solution.

Biologically active molecules that can be administered intracellularly in therapeutic amounts using the formulation of the present invention include ribosomal RNA, antisense polynucleotide of RNA or DNA, polynucleotide of genomic DNA, cDNA or mRNA that encodes for a therapeutically important protein and anti-cancer genes/drugs. Also, the complex of nucleotides (such as DNA, RNA, cDNA or mRNA etc.) and lipid formulation (which is devoid of glycolipid or phospholipid originally) can be added varied amount of the stock solution that contains mixture of equivalent quantity of glycolipid and phospholipid with varying mole-equivalent. The formulation of the present invention may be blended such that one or more of the representatives thereof may be used in a combination to facilitate entry of the said biologically active molecules into cells/tissues. The said therapeutic formulation may be stored at 0° C.-4° C. until complexed with the biologically active therapeutic molecules. Agents that prevent bacterial growth and increase the shelf life may be included along with reagents that stabilize the preparation, e.g., low concentrations of glycerol, cetrimide, methyl paraben, cetyl pyridinium chloride etc. It is specifically warned that freezing and thawing cycles could cause loss in efficiency of the formulation.

The formulation as disclosed herein, and the biologically active therapeutic molecules may be administered intravenously besides other routes such as intramuscular and intra peritonial. Further, the said formulations may be administered to cells at a ratio of 0.1-0.5 microgram of DNA to 50,000 cells in an, in vitro system. The amount of cationic lipid in the said formulation could be varied from a DODEAC to DNA charge ratio of 1:1 to 8:1 considering a single charge for one DODEAC molecule and one negative charge of a single nucleotide base. The plasmid used is a construct of a cytomegalo virus (CMV) promoter linked to a reporter gene β-galactosidase. The plasmid could be of any construction and the examples provided below are merely to demonstrate the efficiency of the formulations.

The invention further provides a process for the preparation of the said formulation comprising the steps of preparing the dispersion of cationic lipids, co-lipids and rice bran isolated glycolipids and phospholipids in the given ratios as disclosed in the present, invention; contacting said dispersion with a biologically active molecule to form a complex between DODEAC and the said biologically active molecules (such as a plasmid DNA) and contacting the cells with the said complex thereby facilitating transfer of said biologically active molecules into the cells. The present invention also provides with various formulations that facilitate intracellular delivery of biologically active molecules.

The present invention provides pharmaceutical genetic therapy preparations, which include rice-bran glycolipid and/or phospholipid mixture pharmacologic agent and a gene of interest.

The present invention provides a method of treating tumor cells by providing genes, which induce greater cell death in combination with a glycolipid pharmacologic agent possessing possible anticancer effect.

It has been determined that using an glycolipid and/or phospholipid pharmacologic agent in combination with a gene of interest provides a distinct improvement in the efficiency of gene delivery to cancer cells which possibly express receptors showing affinity to these glycolipids as well as increasing the number of cells receiving the gene. In particular, glycolipids, and/or phospholipids at mole ratios up to 20 compared to the total lipid, has been shown to facilitate the non-viral gene delivery of a variety of genetic constructs capable of performing their function (including apoptotic cell death) in human cancer cells.

In the present invention, genes which can induce cell death are delivered via a non-viral route in combination with glycolipid/phospholipid pharmacological compounds in order to provide more complete tumor remission and more effective prevention of tumor recurrence, thus leading to improved patient survival. The glycolipid phospholipid pharmacological agent is to be administered via the same route of gene delivery, by incorporating it with the non-viral gene carrier. Here the gene carrier is cationic lipid capable of making liposomes and can form electrostatic complex with negatively, charged DNA/genes. By using these cationic lipid-based carriers, four classes of genes can be delivered:—

1. cytotoxic genes such as tumor necrosis factor alpha (TNFα) or the tumor suppressor gene p53, which promotes apoptosis, can be provided.
2. genes which sensitize cells by enzymatically activating pro-drugs can be provided. For example, thymidine kinase or cytosine deaminase, which respectively activates the cytotoxic pro-drugs gancylclovir and 5-fluorocytosine, could be provided.
3. genes which promote immune surveillance could be provided. For example, tumor growth factor-beta 1 could be provided in combination with interleukin-2 and interferon-gamma.
4. anti-metastatic genes, such as 5 E1A, could be delivered.

Cancer Cell-Specific Gene Delivery Properties of the Rice-Bran Glycolipid-Cationic Liposomal Formulation The in vitro transfection efficacies of cationic lipid formulation containing glycolipid and or phospholipid in combination with DODEAC as cationic lipid and cholesterol as co-lipid at different mote ratios were evaluated by reporter gene expression assay using pCMV-SPORT-β-gal plasmid as the reporter gene in A549, MCF-7 and CHO cells across different cationic lipid: DNA charge ratios. DNA being negatively charged can make electrostatic complex with positively charged cationic lipids in aqueous solution at different charge ratios. The fixed amount of DNA that was used in each data point was 0.3 μg. Further, the cationic Liposome contains DODEAC and CHOL in a mole ratio of 1:1. DNA was mixed with cationic Liposome at indicated charge ratios (+/−) to form cationic lipid/DNA complex. To the resulting cationic lipid/DNA complex the premixed 1:1 mixture of glycolipid and phospholipid cocktail (RG) was added. For experimentations, overall lipid mole ratios of 6:1:1 and 12:1:1 (RG:DODEAC:CHOL) were maintained. This cocktail mixture of cationic lipid/DNA complex and RG lipid was finally added to MCF-7 cells (human breast cancer cells) for gene transfection. The rice bran glycolipid/phospholipids supplemented DODEAC:CHOL (i.e., RG:DODEAC:CHOL) is significantly more efficient (2-5 fold, p<0.001) in transfecting MCF-7 cells than when the cells are transfected with cationic lipid without supplemented with rice bran isolated lipids (i.e. DODEAC:CHOL) or a well known transfection reagent DTDEAC (N,N-di-n-tetradecyl-N,N-dihydroxyethyl ammonium chloride): CHOL already patented by scientists of this laboratory [U.S. Pat. Nos. 6,333,433 B1, 6,346,516 B1, 6,503,945, 6,541,649] (FIG. 1).

The glycolipids or phospholipids isolated from rice bran gums were also mixed individually with DODEAC and cholesterol in different mole ratios to form individual liposomes and tested for its efficacy in MCF-7 cells. The glycolipid and phospholipid containing cationic liposome formulation were designated respectively as 'GLY:DODEAC:CHOL' or 'PHOS:DODEAC:CHOL'. Both these rice-bran isolated natural lipid containing formulations are at least 3 fold more efficient in delivering genes to MCF-7 cells, [p<0.002 and p<0.0001 respectively for GLY:DODEAC:CHOL and PHOS:DODEAC:CHOL with respect to DODEAC:CHOL] (FIG. 2).

Similarly, the premixed cocktail (1:1) of glycolipids and phospholipids isolated from rice bran gums was added to lipid-DNA complex of DODEAC:CHOL and DNA. This was then delivered to A549, human lung cancer metastatic cell line. We observed similar effect as we had seen in case of breast cancer cell line, MCF-7. The resultant RG:DODEAC:CHOL formulation is at least 4 fold more efficient in delivering genes to lung cancer cells when compared to DODEAC:CHOL formulation [p<0.00001] (FIG. 3).

However, significantly low levels of reporter gene expression were observed for RG:DODEAC:CHOL in the otherwise highly transfectable, non-cancerous, transformed cell CHO (FIG. 4) and the transfection efficiency between RG:DODEAC:CHOL and DODEAC:CHOL was statistically insignificant [p>0.01].

The significance of including rice-bran glycolipids and phospholipids in various formulations is very much evident while comparing FIGS. 1-4. The results strongly suggest that the natural glycolipids and phospholipids'isolated from rice bran gums do have selective affinity to cancer cells through yet uncharacterized receptors in cancer cells.

The RG:DODEAC:CHOL formulation was also tested for its sustenance of gene delivery efficacy in MCF-7 cells (breast cancer cells) through varied concentration of serum. The result is important to know because this experiment would be a test for the maintenance of gene delivery efficacy in the tumor model set up in animals. The result (FIG. 5) shows that RG:DODEAC:CHOL maintained its gene delivery efficiency through all the serum concentration studied and most importantly the highest transfection efficiency was maintained for a serum concentration between 40-60%, which is the most relevant serum concentration that is maintained in usual physiological setup.

Thus, the results summarized in FIGS. 1-5 provided strong evidence for the involvement of glycolipids and phospholipids isolated from rice bran gums in selectively targeting gene delivery vehicles to breast and lung cancer cells without showing selective targeting to non-cancerous cells.

Applications

The process of the present invention can be exploited for preparing cationic lipid based gene transfer reagents containing rice-bran isolated glycolipid/phospholipids in the formulation. The invention of this glycolipid/phospholipid associated cationic lipid based gene delivery vehicles are useful for delivering polyanions, polypeptides or nucleopolymers into cancer cells, specifically breast and lung cancer cells. The formulation disclosed herein can be used to deliver an expression vector into a cell for manufacturing or therapeutic use. The expression vectors can be used in gene therapy protocols to deliver a therapeutically useful protein to a cell or for delivering nucleic acids encoding therapeutically useful protein molecules. The formulations using glycolipids/phospholipids associated lipids can be used with anionic, zwitterionic and lipophilic therapeutic agents including anticancer agents such as dokorubicin hydrochloride, a hydrophilic compound, or Taxol™, a lipophilic compound to obtain complexes comprising the invented glycolipid/phospholipid-associated formulation and a therapeutic agent(s).

In particular, the presently disclosed rice bran glycolipid/phospholipids-associated cationic lipid based formulations hold potential for future exploitation in delivering anti-cancer genes/drugs to any cancer but without eliciting treatment related toxicity to normal cells.

EXAMPLES

Examples

The following examples are given by way of illustration therefore should not be construed to limit the scope of the invention.

Materials Used

Dulbecco's Modified Eagle medium (DMEM), fetal bovine serum was obtained from Sigma-Aldrich. p-CMV-.beta.-galactosidase was a generous gift from Dr N. M. Rao, CCMB, India Cell Lines Used Cell-Culture—

MCF-7, CHO, A549 cells were purchased from National Center for. Cell Sciences (Pune, India) and were mycoplasma free Cells were cultured in DMEM medium (Sigma Chemical Co., St. Louis, Mo.) containing 10% fetal bovine serum (Sigma Chemical Co., St. Louis, Mo.) and 1% penicillin-streptomycin at 37° C. in a humidified atmosphere of 5% $CO_2$ in air. Cultures of 85-90% confluency were used for all of the experiments. The cells were trypsinized, counted, sub-cultured in 96-well plates for transfection and viability studies. The cells were allowed to adhere overnight before they were used for experiments.

Example 1

To 600 gins of crude rice bran oil obtained from M/s. Ramcharan Oil Industries, Hyderabad as a gift) having phosphorus content 355 ppm, free fatty acid content of 7.2%, thirty milliliters (30 ml) of water having 95° C. was added and stirred vigorously for a period of 30 minutes using a mechanical stirrer to form a stable emulsion. The emulsion was allowed to settle for two hours and then centrifuged at seven thousand rpm for 30 minutes. The gums were collected and the supernatant oil was subjected to similar treatment one more time. The gums collected at both the steps were collected and subjected to hexane washing two times by dispersing in hexane and centrifuging at 7000 r.p.m. for 30 minutes. The gums thus collected were dried completely using a lyophilizer under vacuum at (–) 110° C. for 24. Around 0.60 grams of dried gums were absorbed on to a silicic acid column. The neutral lipids (0.10 g) were eluted using hexane and ethyl acetate by gradually increasing the polarity up to a 75:25 (hexane:ethyl acetate) mixture. The glycolipids (0.39 g) were then eluted with acetone. Then the column was eluted with methanol to collect the phospholipids (0.10 g).

Example 2

Liposome Preparation All the necessary compounds (DODEAC, Cholesterol, glycolipids and phospholipids) were taken as stock solutions and mixed in different proportions. An average molecular weight of 800 for glycolipid and phospholipid was considered for making these formulations. In order to make the first type of formulation, 1 ml liposomal solution of DODEAC:CHOL (1 mM:1 mM) formulation 645 µg of DODEAC and 386 µg of CHOL were used. The constituent lipids were typically taken in chloroform. The lipids were then dried as a thin film in gentle nitrogen flow for 10 min in ambient temperature of 27° C. and further dried in high vacuum for 6 hrs. Then it was hydrated overnight. After that it was subjected to mild vortexing for 2 min in room temperature and then the solution was undergone bath sonication for maximum of 15 min and then probe sonication at ambient temperature using a Ti-probe sonicator for 3 min to get small unilamellar vesicles (SUV) liposome. A cocktail stock of glycolipid and phospholipids was also made separately. For this, typically 100 mg each of glycolipid and phospholipids were taken in chloroform (5 ml), dried and then suspended in 2 ml of water. This resulted in a thick suspension of glycolipid/phospholipid cocktail [RG]. To the 0.1 ml aqueous solution of DODEAC; CHOL [RG]. (1 mM:1 mM) liposome, 4.8 mg (96 □l) or 9.6 mg (192 □l) of glycolipid/phospholipid cocktail [RG] was added to get a typical molar, ratios of 6:1:1 or 12:1:1 (RG:DODEAC:CHOL) respectively.

For second type of pre-formulated Liposomes (such as DODEAC:CHOL, or GLY:DODEAC:CHOL, or PHOS:DODEAC:CHOL) the lipids in individual chloroform stock solutions were premixed maintaining a final mole ratio of 1:1:0.5. They were dried as a thin film in gentle nitrogen flow for 10 min in ambient temperature of 27° C. and further dried in high vacuum for 6 hrs. Then it was hydrated overnight. After that it was subjected to mild vortexing for 2 min in room temperature and then the solution was undergone bath sonication for maximum of 15 min and then probe sonication at ambient temperature using a Ti-probe sonicator for 3 min to get small unilamellar vesicles (SUV) liposome. The liposomes were kept at 4° C.

Example 3

FIG. 1 is a bar graph showing the influence of the rice bran isolated glycolipid/phospholipids that was supplemented to lipid carrier carrying gene on the expression of a pCMV-β galactosidase construct in MCF-7 human primary breast cancer cells. MCF-7 cells were transfected with a pCMV-β galactosidase reporter construct (0.3 µg) associated in lipoplex form with respective lipid carriers supplemented without (DODEAC:CHOL) or with cocktail mixture of rice-bran isolated glycolipid and phospholipids (RG:DODEAC:CHOL). Together with this DTDEAC:CHOL (our previously patented gene delivery liposomal formulation) was also tested for its transfection efficacy. β galactosidase expression was assessed 48 h post transfection. Each value represents the mean±SEM for three identically treated samples and * indicates the significant difference between the β galactosidase value obtained from cells transfected with DODEAC:CHOL and RG:DODEAC:CHOL. (p<0.001).

The data shows that RG:DODEAC:CHOL formulations could achieve more gene transfection in MCF-7 cells than when RG is not incorporated. The gene transfection by RG:DODEAC:CHOL formulations were even better than DTDEAC:CHOL (our previously patented formulation for efficient gene transfection). This indicates that by incorporation of rice bran glycolipid/phospholipid cocktail [RG] to DODEAC:CHOL formulation, the resulting formulations acquires significantly more gene transfecting ability than the basic formulation DODEAC:CHOL. Hence rice bran glycolipid/phospholipid cocktail probably has the ability to induce more gene transfection capability in cationic liposomes

Example 4

FIG. 2 is a bar graph showing the influence of the rice bran isolated glycolipids or phospholipids that were incorporated along with the cationic lipid/co-lipid on the delivery and expression of a pCMV-β galactosidase gene construct in MCF-7 human primary breast cancer cells. MCF-7 cells were transfected with a pCMV-β galactosidase reporter construct (0.3 μg) associated in lipoplex form with respective lipid carriers supplemented without (DODEAC:CHOL) or with rice-bran isolated glycolipid (GLY:DODEAC:CHOL) or phospholipids (PHOS:DODEAC:CHOL). β galactosidase expression was assessed 48 h post transfection. Each value represents the mean±SEM for three identically treated samples. * indicates the near significant difference between, the β galactosidase value obtained from cells transfected with DODEAC:CHOL and GLY:DODEAC:CHOL (p=0.002) and ** indicates the significant difference between the β galactosidase value obtained from cells transfected with DODEAC:CHOL and PHOS:DODEAC:CHOL (p<0.00005) respectively.

The result shows that even the preformed liposomal formulation containing either phospholipid or glycolipid along with DODEAC and CHOL has significantly more gene transfection ability in MCF-7 cancer cells than the transfection ability of basic DODEAC:CHOL formulation. So, the rice bran phospholipid or glycolipid has individual capability to induce more gene transfection ability of cationic liposomes in cancer cells Example 5

FIG. 3 is a bar graph showing the influence of the rice bran isolated glycolipid/phospholipids that was supplemented to lipid carrier carrying gene on the expression of a pCMV-β galactosidase construct in A549 human lung cancer metastatic cells. A549 cells were transfected with a pCMV-β galactosidase reporter construct (0.3 μg) associated in lipoplex form with respective lipid carriers supplemented without (DODEAC:CHOL) or with cocktail mixture of rice-bran isolated glycolipid and phospholipids (RG:DODEAC:CHOL). β galactosidase expression was assessed 48 h post transfection. Each value represents the mean±SEM for three identically treated samples and * indicates the significant difference between the β galactosidase value obtained from cells transfected with DODEAC:CHOL and RG:DODEAC:CHOL. (p<0.0001)

As was witnessed in breast cancer cells, MCF-7 (Example 3), herein, we observed the similar trend. The data shows that RG:DODEAC:CHOL formulations could achieve more gene transfection in A549 lung cancer cells than when RG is not incorporated. The gene transfection by RG:DODEAC:CHOL formulations were even better than DTDEAC:CHOL (our previously patented formulation for efficient gene transfection). This indicates that by incorporation of rice bran glycolipid/phospholipid cocktail [RG] to DODEAC:CHOL formulation, the resulting formulations acquires significantly more gene transfecting ability than the basic formulation DODEAC:CHOL. Hence rice bran glycolipid/phospholipid cocktail probably has the ability to induce more gene transfection capability in cationic liposomes Example 6

FIG. 4 is a bar graph showing that there is no significant influence of the rice bran isolated glycolipid/phospholipids-associated lipid carrier carrying gene on the expression of a pCMV-β galactosidase construct in CHO (chinese hamster ovarian) transformed cells, which is in originality not a cancer cell line. CHO cells were transfected with a pCMV-β galactosidase reporter construct (0.3 μg) associated in lipoplex form with respective lipid carriers DODEAC:CHOL and cocktail mixture of glycolipid and phospholipids supplemented to lipoplex RG:DODEAC:CHOL. β galactosidase expression was assessed 48 h post transfection. Each value represents the mean±SEM for three identically treated samples. # indicates that the difference between the β galactosidase value obtained from cells transfected with DODEAC:CHOL and RG:DODEAC:CHOL (p>0.01) is not significant as compared to the results obtained in cells with cancer lineage.

CHO cells are transformed to immortality, but do not have cancer lineage. The result in this example shows that the association of glycolipid/phospholipid (RG) to cationic Liposome did not impart any additional increase in gene transfection in CHO cells. This shows that the RG has no specific affinity to non cancer cells and hence is unable to provide any specific targeting ability and gene transfection enhancing ability to Liposomes against non cancer cells Example 7

Figure 5:
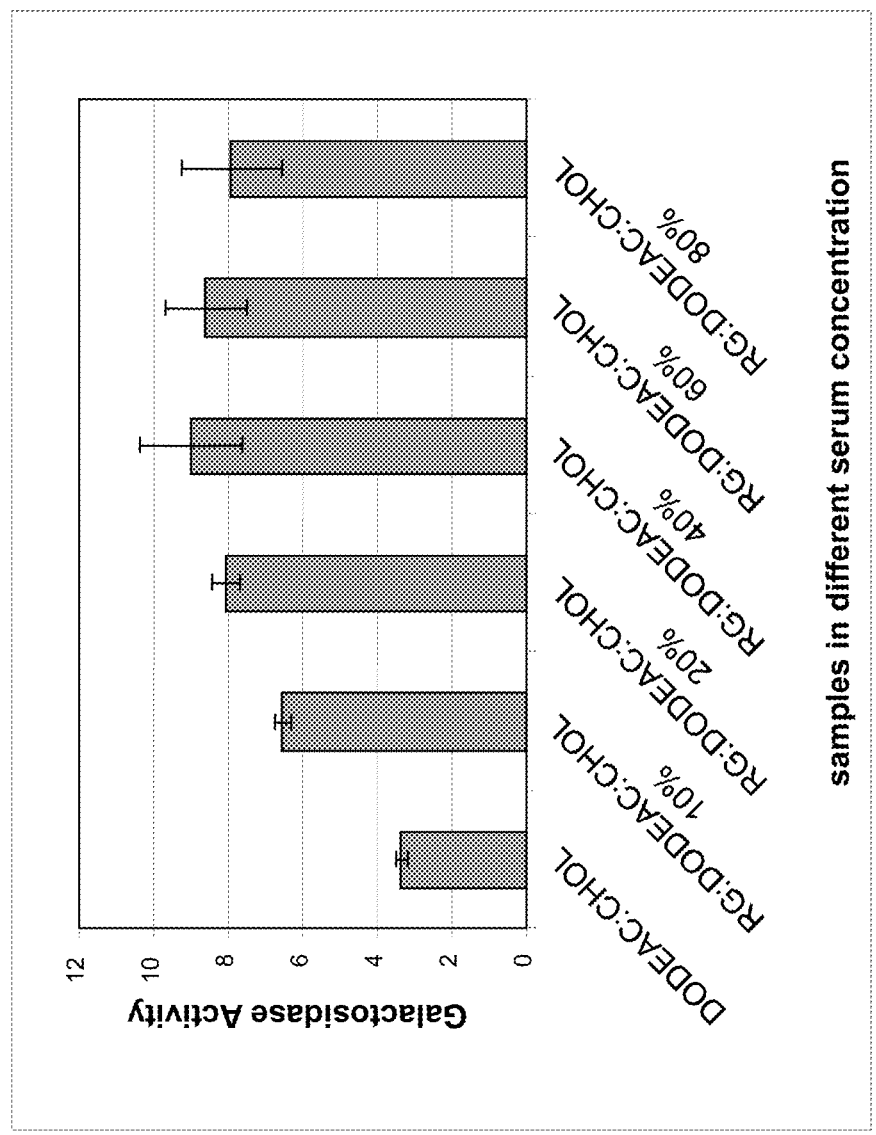

FIG. 5 is a bar graph showing that the gene delivery efficiency in MCF-7, human breast cancer cells, of rice bran isolated glycolipid/phospholipids-associated lipid carrier remains significantly undeterred in varied serum concentration especially in the physiologically relevant serum concentration range between 40-60% (here precision is not necessary, because physiologically the serum concentration varies between person to person, subject to subject of same mammalian species. But, generally speaking it is between 40-60% for almost all mammals. Hence, we included two data points 40% and 60%.). MCF-7 cells were transfected with a pCMV-β galactosidase reporter construct (0.3 μg) associated in lipoplex form with respective lipid carriers supplemented without (DODEAC:CHOL) or with cocktail mixture of rice-bran isolated glycolipid and phospholipids (RG:DODEAC:CHOL) (6:1:1). The RG:DODEAC:CHOL formulated lipoplex was incubated with MCF-7 cells in media containing the final serum concentration of 10%, 20%, 40%, 60% and 80%. The β galactosidase activity was evaluated 48 h-post transfection and expressed as β galactosidase unit per cell. Each value represents the mean±SEM for three identically treated cell wells. There were practically no differences in transfection efficiencies of RG:DODEAC:CHOL formulated lipoplex treated to MCF-7 cells in between the range of 20-80% of serum concentration.

The data clearly indicates that the enhanced transfection efficiency of RG associated lipid-DNA complex is maintained in the relevant physiological condition. Generally, in higher serum concentration, the lipid/DNA complex tend to collapse leading to decrease in gene transfection. This is not happening here in this case. This indicates that the RG-associated formulation maintains its cancer cell selectivity while maintaining its gene transfection efficiency.

Example 8

Gene Transfection with Pre-Formulated Liposomes—

Cells were seeded at a density of 12,000-15,000 cells/well in a 96 well plate usually 24 h before transfection. 0.30 μg of pCMV-SPORT-β-gal DNA (diluted to 50 μl with plain DMEM) was complexed with varying amount of cationic liposomes (diluted to 50 μl with plain DMEM) for 30 min. The molar ratios (cationic lipid:DNA) were 8:1, 4:1, 2:1 and 1:1, although the data were mostly shown for 4:1 or 2:1 cationic lipid:DNA mote ratios. After the complexation was completed, 200 □μl of DMEM containing 10% FBS (CM1X) were added to the resulting lipoplexes for triplicate experiments. Thus the final concentration of serum became 6.7%. Cells were washed with phosphate-buffered saline (PBS), pH 7.4 (1×200 0) and then with lipoplex (100 μl). After incubation of the cell plates at a humidified atmosphere containing 5% $CO_2$ at 37° C. for 4 h, 100 μl of DMEM containing 10% FBS (CM1X) were added to cells. The reporter gene activity was assayed after 48 h. The media were removed completely from the wells and cells were lysed with 50 μl of 1× lysis buffer (NP-40) (Please give the composition of the buffer) for 30 min. The β-galactosidase activity per well was estimated by adding 50 μl of 2× substrate (1.33 mg/ml of ONPG, 0.2 M sodium phosphate, pH 7.3 and 2 mM magnesium chloride) to the cell-lysate in the 96 well plate. Absorption of the product ortho-nitrophenol at 405 nm was converted to absolute β-galactosidase units using a calibration curve constructed with commercial β-galactosidase enzyme.

Example 9

Gene Transfection with Liposomes Supplemented with Cocktail of Glycolipid and Phospholipid—

Cells were seeded at a density of 12,000-15,000 cells/well in a 96 well plate usually 24 h before transfection. The cationic liposomes were serially diluted (diluted to 50 μl it with plain DMEM) and then to it varied volumes of cocktail stock containing glycolipid and phospholipids were added (Pls mention the amount). The mixtures were promptly added to 0.30 μg of pCMV-SPORT-β-gal DNA (diluted to 50 μl with plain DMEM) and were left for complexation for 30 min. The molar ratios (cationic lipid:DNA) were 8:1, 4:1, 2:1 and 1:1, although the data here were mostly shown for 4:1 or 2:1 cationic lipid:DNA mole ratios. To it 200μλ of DMEM containing 10% FBS (CM1X) were added to the resulting lipoplexes for triplicate experiments. Thus the final concentration of serum became 6.7%. Cells were washed with phosphate-buffered saline (PBS), pH 7.4 (1×200 μl) and then with lipoplex (100 μl). After incubation of the cell plates at a humidified atmosphere containing 5% $CO_2$ at 37° C. for 4 h, 1000 of DMEM containing 10% FBS (CM1X) were added to cells. The reporter gene activity was assayed after 48 h. The media were removed completely from the wells and cells were lysed with 50 μl of 1× lysis buffer (NP-40) for 30 min. The β-galactosidase activity per well was estimated by adding 50 of 2× substrate (1.33 mg/ml of ONPG, 0.2 M sodium phosphate, pH 7.3 and 2 mM magnesium chloride) to the cell-lysate in the 96 well plate. Absorption of the product ortho-nitrophenol at 405 nm was converted to absolute β-galactosidase units using a calibration curve constructed with commercial β-galactosidase enzyme.

Example 10

Studying the Dependence of Gene Transfection on Serum Concentration—

Cells were seeded at a density of 12,000-15,000 cells/well in a 96 well plate usually 18-24 h before transfection. The cationic liposomes were serially diluted (diluted to 50 μl with plain DMEM) and then to it varied volumes of cocktail stock containing glycolipid and phospholipids were added. The mixtures were promptly added to 0.30 μg of pCMV-SPORT-β-gal DNA (diluted to 50 μl with plain DMEM) and were left for complexation for 30 min. The molar ratios (cationic lipid:DNA) were 8:1, 4:1, 2:1 and 1:1, although the data here were shown for cationic lipid:DNA mole ratio 4:1 and RG:DODEAC:CHOL mole ratio of 6:1:1 only. To it 200 μl of DMEM containing varied concentration of FBS (CM1X) were added to the resulting lipoplexes for triplicate experiments to get the final serum concentration of 10%, 20%, 40%, 60% and 80%. Cells were washed with phosphate-buffered saline (PBS), pH 7.4 (1×200 0) and then with lipoplex (100 μl). After incubation of the cell plates at a humidified atmosphere containing 5% $CO_2$ at 37° C. for 4 h, the cells were washed with PBS and 200 μl of DMEM containing 10% FBS (CM1X) were added to cells. The reporter gene activity was assayed after 48 h. The media were removed completely from the wells and cells were lysed with 50 μl of 1× lysis buffer (NP-40) for 30 min. The β-galactosidase activity per well was estimated by adding 50 μl of 2× substrate (1.33 mg/ml of ONPG, 0.2 M sodium phosphate, pH 7.3 and 2 mM magnesium chloride) to the cell-lysate in the 96 well plate. Absorption of the product ortho-nitrophenol at 405 nm was converted to absolute β-galactosidase units using a calibration curve constructed with commercial β-galactosidase enzyme.

Example 11

Statistical Analysis—

All experiments were repeated at least thrice. Data were expressed as mean±standard derivation and statistically analyzed by the two-tailed unpaired Student t-test using the Microsoft Excel software program (Microsoft, Seattle, Wash.). Data were primarily considered significant if $p<0.001$.

ADVANTAGES OF THE PRESENT INVENTION

1. This formulation did not, mediate efficient delivery of genes to non-cancerous cells, but showed highly efficient and enhanced gene transfection in cancer cells. This show the potential use of this formulation to deliver anticancer therapeutics to cancer cells without eliciting treatment related toxicity to normal cells.
2. This newly developed glycolipid/phospholipid (RG)-associated cationic liposomal formulation gave us a new observation that upon associating RG with cationic liposomes, the liposomal gene delivery agent possesses cancer cell selectivity and enhanced transfection in cancer cells. We hypothesize that any gene transfecting cationic liposome upon associating with RG will show cancer selectivity and enhanced gene transfection in cancer cells.
3. In physiologically relevant serum condition, where most of the cationic lipid/DNA complex collapse down, this formulation maintains its enhanced gene transfection efficiency.

The invention claimed is:
1. A liposomal formulation for selective targeting and delivery of genes or genetic products to cancer cells, comprising:
    (a) a gene or genetic product;
    (b) a cationic lipid in the range of 7-40 mole % of all constituent lipids;
    (c) a co-lipid in the range of 7-40 mole % of all constituent lipids, the co-lipid being capable of facilitating an intracellular delivery of the gene or genetic product to cancer cells; and
    (d) rice bran glycolipids and, optionally, rice bran phospholipids, as adjuvant lipids in the range of 20-85 mole % of all constituent lipids, the adjuvant lipids being capable of enhancing the transfection efficiency of the formulation and effectively enable selective delivery of the gene or genetic product to cancer cells.

2. The formulation of claim 1, wherein the cationic lipid is selected from the group consisting of DODEAC (N,N-di-n-octadecyl-N,N-dihydroxyethyl ammonium chloride), DOTAP (N-[1-(2,3-Dioleoyloxy)propyl]-N,N,N-trimethylammonium methylsulfate (or chloride)), and DMRIE (2,3-di(myristyloxy)propyl-[2-hydroxyethyl]-dimethylammonium bromide).

3. The formulation of claim 1, wherein the co-lipid is a natural sterol.

4. The formulation of claim 1, wherein the co-lipid is cholesterol.

5. The formulation of claim 1, wherein the rice bran glycolipids and the rice bran phospholipids are isolated from rice bran oil gums.

6. The formulation of claim 1, wherein the genetic product is selected from the group consisting of p53, tumor necrosis factor, thymidine kinase, cytosine deaminase, 5 EIA, and TGF-beta.

7. A process for the preparation of the formulation of claim 1, wherein the process is:
   a) process (A) comprising the steps of:
      i) mixing glycolipids and phospholipids isolated from rice bran oil gums in a mole ratio of 1:1 in a solvent, preferably chloroform, followed by drying and thereafter suspending in water to obtain suspension of glycolipid-phospholipid cocktail (RG);
      ii) mixing cationic lipid, preferably DODEAC and a co-lipid, preferably cholesterol in a mole ratio of 1:1 in a solvent, preferably chloroform, followed by drying as a thin film by nitrogen flow for a period ranging between 10-15 min at temperature ranging between 25-30° C. and further drying the thin film under vacuum for a period ranging between 4-6 hrs to obtain a dried lipid film;
      iii) hydrating the dried lipid film as obtained in step (b) by keeping the dried film in water for a period ranging between 10-12 hrs, followed by vortexing for a period ranging between 1-2 min, bath sonicating for a period ranging between 2-3 min, and probe sonicating for a period ranging between 2-3 min at a temperature ranging between 25-30° C. to produce an aqueous solution of cationic lipid; and
      iv) adding the aqueous solution of a cationic lipid, as obtained in step (c), into the glycolipid-phospholipid cocktail (RG) as obtained in step (a) while maintaining the mole ratio of RG:cationic lipid:co-lipid in the range of 6:1:1 to 12:1:1 to obtain the formulation; or
   b) process (B) comprising the steps of:
      i) mixing a cationic lipid, preferably DODEAC, a co-lipid, preferably cholesterol, and a glycolipid or a phospholipid individually or glycolipid-phospholipid cocktail (RG), in a mole ratio of 1:1:0.5 in a solvent, preferably chloroform, wherein the RG is obtained by mixing glycolipids and phospholipids isolated from rice bran oil gums in a mole ratio of 1:1 in a solvent, preferably chloroform, followed by drying and thereafter suspending in water to obtain a suspension of RG; followed by
      ii) drying the mixture as a thin film by nitrogen flow for a period ranging between 10-15 min at a temperature ranging between 25-30° C.,
      iii) drying the thin film under vacuum for a period ranging between 4-6 hrs to obtain a dried lipid film; and
      iv) hydrating the dried lipid film by keeping the dried lipid film in water for a period ranging between 10-12 hrs, followed by vortexing for a period ranging between 1-2 min, bath sonicating for a period ranging between 2-3 min, and probe sonicating for a period ranging between 2-3 min at a temperature ranging between 25-30° C. to obtain the formulation.

8. The formulation of claim 1, wherein the formulation has the mole ratio of a rice bran glycolipid-phospholipid cocktail (RG):cationic lipid:co-lipid in the range of from 6:1:1 to 12:1:1.

* * * * *